United States Patent
Urata (10) Patent No.: US 11,452,195 B2
(45) Date of Patent: Sep. 20, 2022

(54) X-RAY DEVICE

(71) Applicant: Shimadzu Corporation, Kyoto (JP)

(72) Inventor: Tomoaki Urata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 77 days.

(21) Appl. No.: 17/268,370

(22) PCT Filed: Jun. 25, 2019

(86) PCT No.: PCT/JP2019/025146
§ 371 (c)(1),
(2) Date: Feb. 12, 2021

(87) PCT Pub. No.: WO2020/054174
PCT Pub. Date: Mar. 19, 2020

(65) Prior Publication Data
US 2021/0195722 A1    Jun. 24, 2021

(30) Foreign Application Priority Data

Sep. 11, 2018  (JP) .............................. JP2018-169769

(51) Int. Cl.
*H05G 1/54*    (2006.01)
*H05G 1/34*    (2006.01)

(52) U.S. Cl.
CPC .................................... *H05G 1/34* (2013.01)

(58) Field of Classification Search
CPC ... H05G 1/34; H05G 1/26; H05G 1/54; A61B 6/00
See application file for complete search history.

(56) References Cited

U.S. PATENT DOCUMENTS 6,426,997 B1 *   7/2002  Fuchs ..................... H05G 1/34
                                                        378/118
2019/0317144 A1 * 10/2019 Xu ........................ H01J 35/025

FOREIGN PATENT DOCUMENTS

JP         2006-100174 A      4/2006

OTHER PUBLICATIONS

Written Opinion by the International Search Authority for PCT application No. PCT/JP2019/025146, dated Sep. 17, 2019, submitted with a machine translation.

* cited by examiner

*Primary Examiner* — Jurie Yun
(74) *Attorney, Agent, or Firm* — Muir Patent Law, PLLC (57) ABSTRACT

An X-ray device includes a degree-of-wear detection unit for detecting a degree-of-wear of an emitter, an adhesion amount estimation unit for estimating an adhesion amount of a conductive material onto an envelope based on the degree-of-wear of the emitter and a relation between the degree-of-wear of the emitter and an adhesive amount of the conductive material onto the envelope stored in a storage unit.

7 Claims, 7 Drawing Sheets

X-RAY DEVICE

TECHNICAL FIELD

The present invention relates to an X-ray device provided with an X-ray generation unit in which an emitter and a target are disposed within an envelope.

BACKGROUND ART

As a life of an X-ray generation unit provided with an X-ray tube, a discharge life of an X-ray tube can be exemplified. For example, for a space discharge caused by a decrease in the vacuum degree of an X-ray tube, the risk of a discharge is conventionally predicted from the vacuum degree of the X-ray tube (see Patent Document 1). Further, the risk of a discharge is predicted by the number of exposures of X-rays from an X-ray generation unit.

PRIOR ART DOCUMENT

Patent Document

Patent Document 1: Japanese Unexamined Patent Application Publication No. 2006-100174

SUMMARY OF THE INVENTION

Problems to be Solved by the Invention

As a discharge causing a discharge life of an X-ray tube, not only a space discharge caused by the decrease in the degree of vacuum of the X-ray tube but also a creeping discharge caused by adhesion of a conductive material constituting the emitter onto to the inner peripheral surface of the envelope constituting the X-ray tube can be exemplified. Regarding the creeping discharge caused by the adhesion of the conductive material constituting the emitter onto the inner surface of the envelope, it is difficult to predict the risk. In a case where the risk of the discharge is predicted by the number of exposure times of the X-rays from the X-ray generation unit, the risk of discharge differs depending on the X-ray condition, such as, e.g., the tube voltage, the tube current, and the exposure time at the time of the X-ray exposure, so that the prediction accuracy of the risk becomes inaccurate.

The present invention has been made to solve the above-described problems, and an object of the present invention is to provide an X-ray device capable of more accurately estimating an adhesion amount of a conductive material constituting an emitter onto an envelope.

Means for Solving the Problem

According to a first aspect of the invention, an X-ray device includes:
 an X-ray generation unit including an emitter made of a conductive material, the emitter being configured to emit electrons, a target for generating X-rays by being collided by the electrons emitted from the emitter, and an envelope accommodating the emitter and the target;
 a degree-of-wear detection unit configured to detect a degree-of-wear of the emitter;
 a storage unit configured to store a relation between the degree-of-wear of the emitter and an adhesion amount of the conductive material constituting the emitter onto the envelope; and
 an adhesion amount estimation unit configured to estimate the adhesion amount of the conductive material constituting the emitter onto the envelope based on the degree-of-wear of the emitter and a relation between the degree-of-wear of the emitter and the adhesion amount of the conductive material constituting the emitter stored in the storage unit.

That is, the X-ray device according to the first aspect of the invention is provided with an X-ray generation unit including an emitter made of a conductive material, the emitter being configured to emit electrons, a target for generating X-rays by being collided by the electrons emitted from the emitter, an envelope accommodating the emitter and the target, a storage unit configured to store a relation between the degree-of-wear of the emitter and an adhesion amount of the conductive material constituting the emitter onto the envelope, a processor for executing the following processing. (1) The degree-of-wear of the emitter is detected. (2) An adhesion amount of the conductive material constituting the emitter onto the envelope is estimated based on the degree-of-wear of the emitter and the relation between the degree-of-wear of the emitter and the adhesion amount of the conductive material constituting the emitter stored in the storage unit.

According to a second aspect of the invention, the degree-of-wear detection unit detects the degree-of-wear of the emitter from a voltage, a current, or an energization time of the emitter.

That is, the processor executes the processing of detecting the degree-of-wear of the emitter from a voltage, a current, or an energization time of the emitter.

According to a third aspect of the invention, the X-ray device further includes a temperature sensor, wherein the adhesion amount estimation unit estimates the adhesion amount of the conductive material constituting the emitter onto the envelope by utilizing a temperature of the X-ray generation unit or a temperature of an insulation oil in the X-ray generation unit detected by the temperature sensor.

That is, the processor performs the processing of estimating the adhesion amount of the conductive material constituting the emitter onto the envelope by utilizing the temperature of the X-ray generation unit or the temperature of the insulation oil in the X-ray generation unit detected by the temperature sensor.

According to a fourth aspect of the invention, an attitude sensor configured to detect an attitude of the X-ray generation unit is further provided, wherein the adhesion amount estimation unit estimates the adhesion amount of the conductive material constituting the emitter onto the envelope by utilizing the attitude of the X-ray generation unit detected by the attitude sensor.

That is, the processor executes the processing of estimating the adhesion amount of the conductive material constituting the emitter onto the envelope by utilizing the attitude of the X-ray generation unit detected by the attitude sensor.

According to a fifth aspect of the invention, the storage unit further stores a relation between the adhesion amount of the conductive material constituting the emitter onto the envelope and a probability of occurrence of a creeping discharge onto the envelope, and the X-ray device further comprises a creeping discharge estimation unit configured to estimate the probability of occurrence of the creeping discharge based on the degree-of-wear of the emitter, the relation between the degree-of-wear of the emitter and the adhesion amount of the conductive material constituting the emitter stored in the storage unit, and a relation between the adhesion amount of the conductive material constituting the emitter onto the envelope and the probability of occurrence of the creeping discharge onto the envelope stored in the storage unit.

That is, the storage unit further stores the relation between the adhesion amount of the conductive material constituting the emitter onto the envelope and the probability of occurrence of the creeping discharge to the envelope, and the processor executes the processing of estimating of the probability of occurrence of the creeping discharge based on the degree-of-wear of the emitter, the relation between the degree-of-wear of the emitter and the adhesion amount of the conductive material constituting the emitter stored in the storage unit, and a relation between the adhesion amount of the conductive material constituting the emitter onto the envelope and the probability of occurrence of the creeping discharge onto the envelope stored in the storage unit.

According to a sixth aspect of the invention, when the probability of occurrence of the creeping discharge estimated by the creeping discharge estimation unit exceeds a preset value, a warning display is performed.

That is, the processor executes the processing of performing a warning display when the probability of occurrence of a creeping discharge estimated by the creeping discharge estimation unit exceeds a preset value.

According to a seventh aspect of the invention, the storage unit further stores a relation between the adhesion amount of the conductive material constituting the emitter onto the envelope and a transmission rate of the X-rays passing through the envelope, or a relation between the adhesion amount of the conductive material constituting the emitter onto the envelope and a spectrum of the X-rays passing through the envelope, and the X-ray device further comprises an image processing unit configured to change an image processing condition of the X-ray image to be display on a display unit based on the adhesion amount of the conductive material constituting the emitter onto the envelope and, a relation between the adhesion amount of the conductive material constituting the emitter onto the envelope and the transmission rate of the X-rays passing through the envelope stored in the storage unit or a relation between the adhesion amount of the conductive material constituting the emitter onto the envelope and a spectrum of the X-rays passing through the envelope stored in the storage unit.

That is, the storage unit further stores a relation between the adhesion amount of the conductive material constituting the emitter onto the envelope and a transmission rate of the X-rays passing through the envelope, or a relation between the adhesion amount of the conductive material constituting the emitter onto the envelope and a spectrum of the X-rays passing through the envelope, and the X-ray device further includes a processor for performing the processing of changing an image processing condition of the X-ray image to be displayed on a display unit based on the adhesion amount of the conductive material constituting the emitter onto the envelope, a relation between the adhesion amount of the conductive material constituting the emitter onto the envelope and the transmission rate of the X-rays passing through the envelope stored in the storage unit, or a relation between the adhesion amount of the conductive material constituting the emitter onto the envelope and a spectrum of the X-rays passing through the envelope stored in the storage unit.

Effects of the Invention

According to the first and second aspects of the invention, it is possible to estimate the adhesion amount of the conductive material constituting the emitter onto the envelope based on the degree-of-wear of the emitter.

According to the third aspect of the invention, it is possible to accurately estimate the adhesion amount of the conductive material constituting the emitter onto the envelope by utilizing the temperature of the X-ray generation unit or the temperature of the insulation oil detected by the temperature sensor.

According to the fourth aspect of the invention, by utilizing the attitude of the X-ray generation unit detected by the attitude sensor, it is possible to more accurately estimate the adhesion amount of the conductive material constituting the emitter onto the envelope considering the temperature distribution due to the attitude of the X-ray generation unit.

According to the fifth and sixth aspects of the invention, based on the degree-of-wear of the emitter, it is possible to estimate the probability of occurrence of a creeping discharge. By utilizing it, it is possible to warn that the discharging life is approaching.

According to the seventh aspect of the invention, it is possible to recognize the transmission rate of X-rays passing through the envelope or the spectrum of the X-rays passing through the envelope based on the degree-of-wear of the emitter. With this, it is possible to display an appropriate image by the display by changing the image processing condition of the X-ray image to be displayed on the display unit.

EMBODIMENTS FOR CARRYING OUT THE INVENTION

Figure 1:
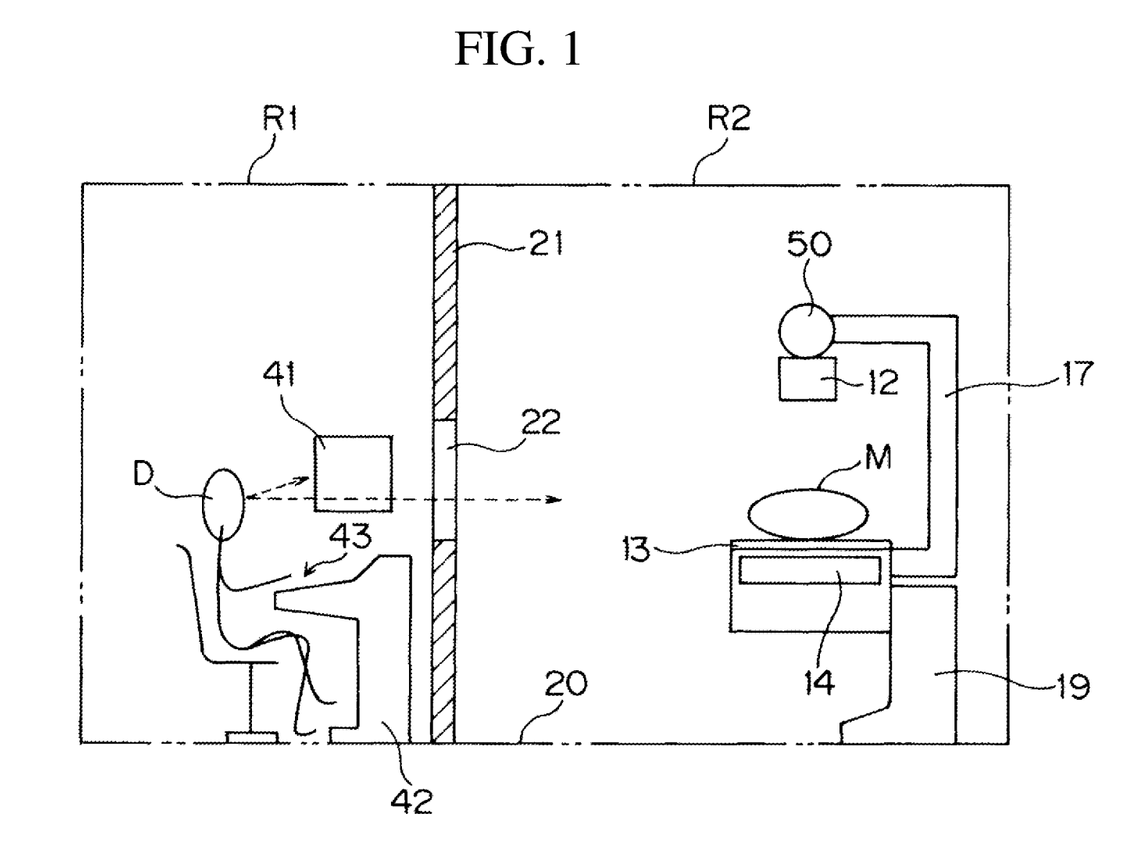
FIG. 1 is a schematic diagram of an X-ray fluoroscopic imaging apparatus constituting a part of an X-ray device according to the present invention.
Figure 2:
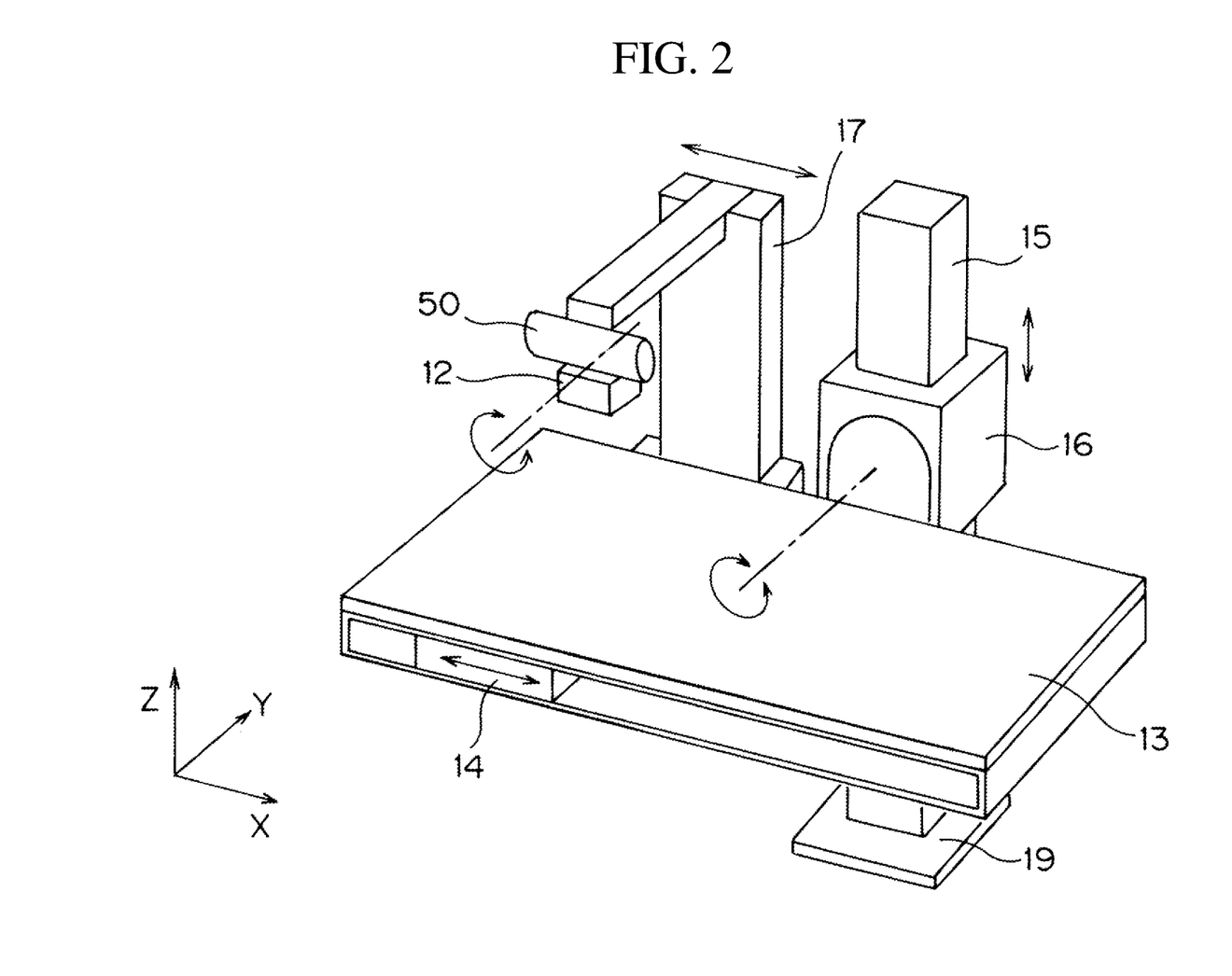
FIG. 2 is a perspective view of a fluoroscopic imaging table disposed within an examination room R2.

Hereinafter, some embodiments of the present invention will be described with reference to the attached drawings. FIG. 1 is a schematic diagram of an X-ray fluoroscopic imaging apparatus constituting a part of an X-ray device according to the present invention. FIG. 2 is a perspective view of a fluoroscopic imaging table arranged in an examination room R2.

The X-ray imaging apparatus is for performing X-ray imaging and X-ray fluoroscopy on a subject M and is provided with a controller 42 with an operation panel 43 installed in an operating room R1, a display unit 41, and a fluoroscopic imaging table installed in an examination room R2. The operating room R1 and the examination room R2 are separated from each other by a partition wall 21. The partition wall 21 is provided with a lead glass window 22 capable of blocking X-rays, and an operator D can confirm the state of the inside of the examination room R2 through the lead glass window 22.

As shown in FIG. 2, the X-ray fluoroscopic imaging table installed in the examination room R2 is provided with a main support 15 vertically extended from a base 19, a holding unit 16 provided so as to be vertically movable with respect to the main support 15, a top board 13 rotatably connected to the holding unit 16, a support 17 supporting an X-ray generation unit 50 and a collimator 12, and an X-ray detector 14, such as, e.g., a flat panel detector, disposed at a position facing the X-ray generation unit 50 below the surface of the top board 13. Note that in FIG. 1, the illustrations of the main support 15 and the holding unit 16 are omitted.

The holding unit 16 moves up and down in the Z-direction shown in FIG. 2. Further, the top board 13 rotates about an axis perpendicular to the longitudinal direction of the top board 13 and extending in the horizontal direction (axis extending in the Y-direction shown in FIG. 2), together with the support 17. Further, the support 17 and the X-ray detector 14 reciprocally move in synchronization with each other in the longitudinal direction of the top board 13. Note that the X-ray generation unit 50 and the collimator 12 are configured to move up and down in the Z-direction shown in FIG. 2 together with the support 17. Note that the X-ray generation unit 50 and the collimator 12 are configured to rotate in accordance with the rotation of the top board 13 and the support 17 and is swingable in a state of being supported by the support 17. The X-ray generation unit 50 changes in the attitude in accordance with the swinging motion to the support 17 and the rotation of the support 17.

Figure 3:
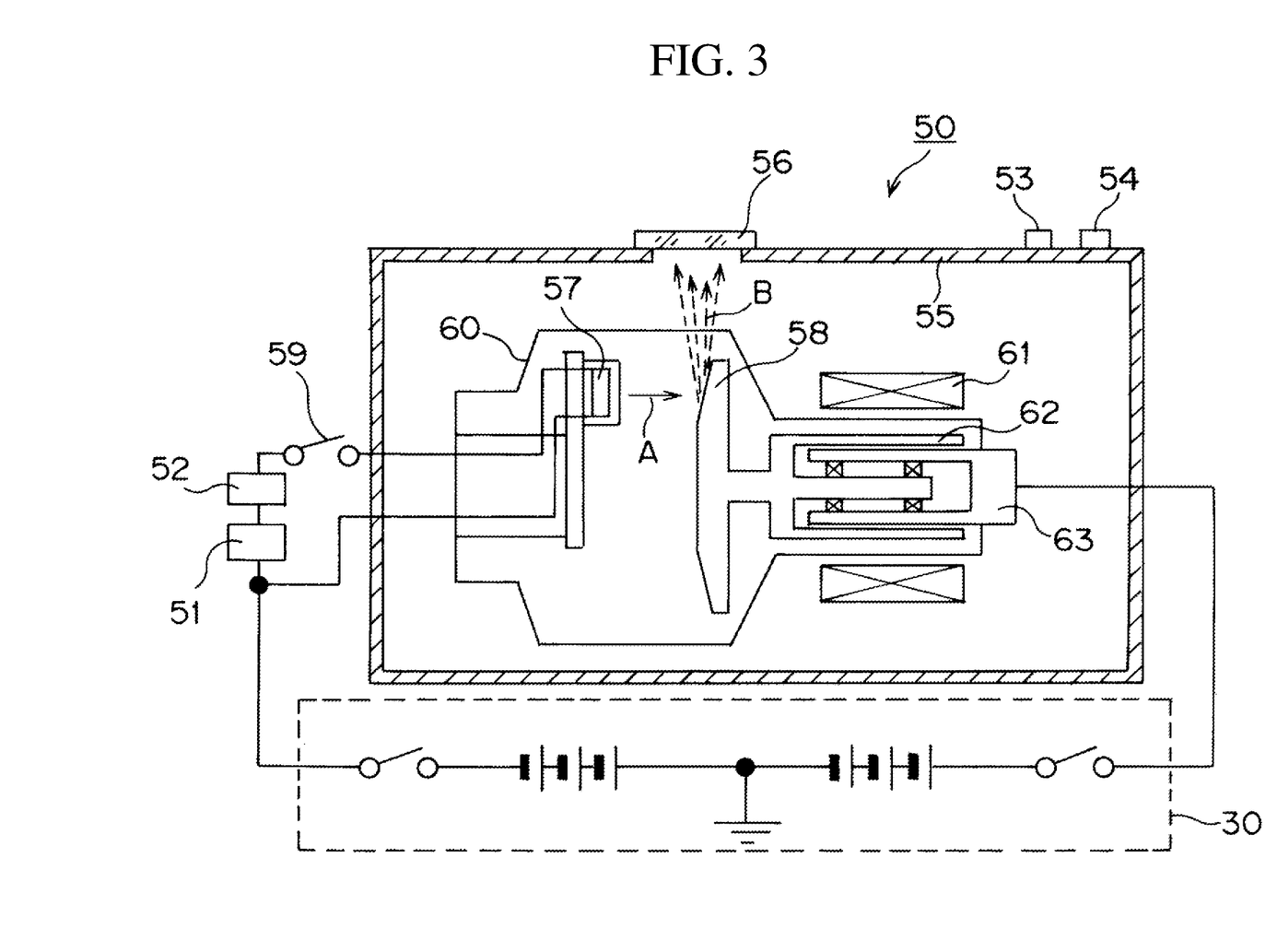
FIG. 3 is a schematic diagram showing the configuration of an X-ray generation unit 50.

FIG. 3 is a schematic diagram showing the configuration of the X-ray generation unit 50.

This X-ray generation unit 50 has a configuration in which an emitter 57 as a cathode and a target 58 which is a rotatable anode are arranged in an insulating envelope 60 made of glass or ceramic. The envelope 60 is vacuumed. The envelope 60 is disposed in a casing 55 having an X-ray transmission window 56, and the casing 55 is made of an X-ray non-transmissive material such as lead. The casing 55 is filled with an insulation oil. Further, the temperature sensor 53 for measuring the temperature of the insulation oil is provided outside the casing 55. Furthermore, an attitude sensor 54, such as, e.g., an accelerometer, for detecting the attitude of the X-ray generation unit 50, which changes in the attitude with the swinging motion to the support 17 or the rotation of the support 17, is provided outside the casing 55.

The emitter 57 is referred to also as a filament and is connected to an AC power source 51 and an ammeter 52 via a switch 59. Further, the target 58 is rotatably supported by a bearing mechanism 63. Then, the target 58 rotates by the drive of the rotational drive mechanism composed of a motor stator 61 and a motor rotor 62.

This X-ray generation unit 50 is provided with a high-voltage supply unit 30. To the emitter 57, a negative high-voltage is applied by the high-voltage supply unit 30. To the target 58, a positive high-voltage is applied by the high-voltage supply unit 30. With this, a high tube voltage is applied between the emitter 57 and the target 58.

When a current is supplied from the AC power source 51 to the emitter 57 and the emitter 57 is heated by an indirectly heating mechanism (not shown), thermal electrons A are emitted from the emitter 57. The thermal electrons A are moved toward the target 58 by the tube voltage to generate X-rays B by colliding with the target 58. At this time, the current flowing through the emitter 57 is measured by the ammeter 52, and the tube voltage supplied from the high-voltage supply unit 30 is controlled so that the current value becomes constant. From the current value flowing through the emitter 57 and the magnitude of the tube voltage at this time, the degree-of-wear of the emitter 57 is estimated.

Figure 4:
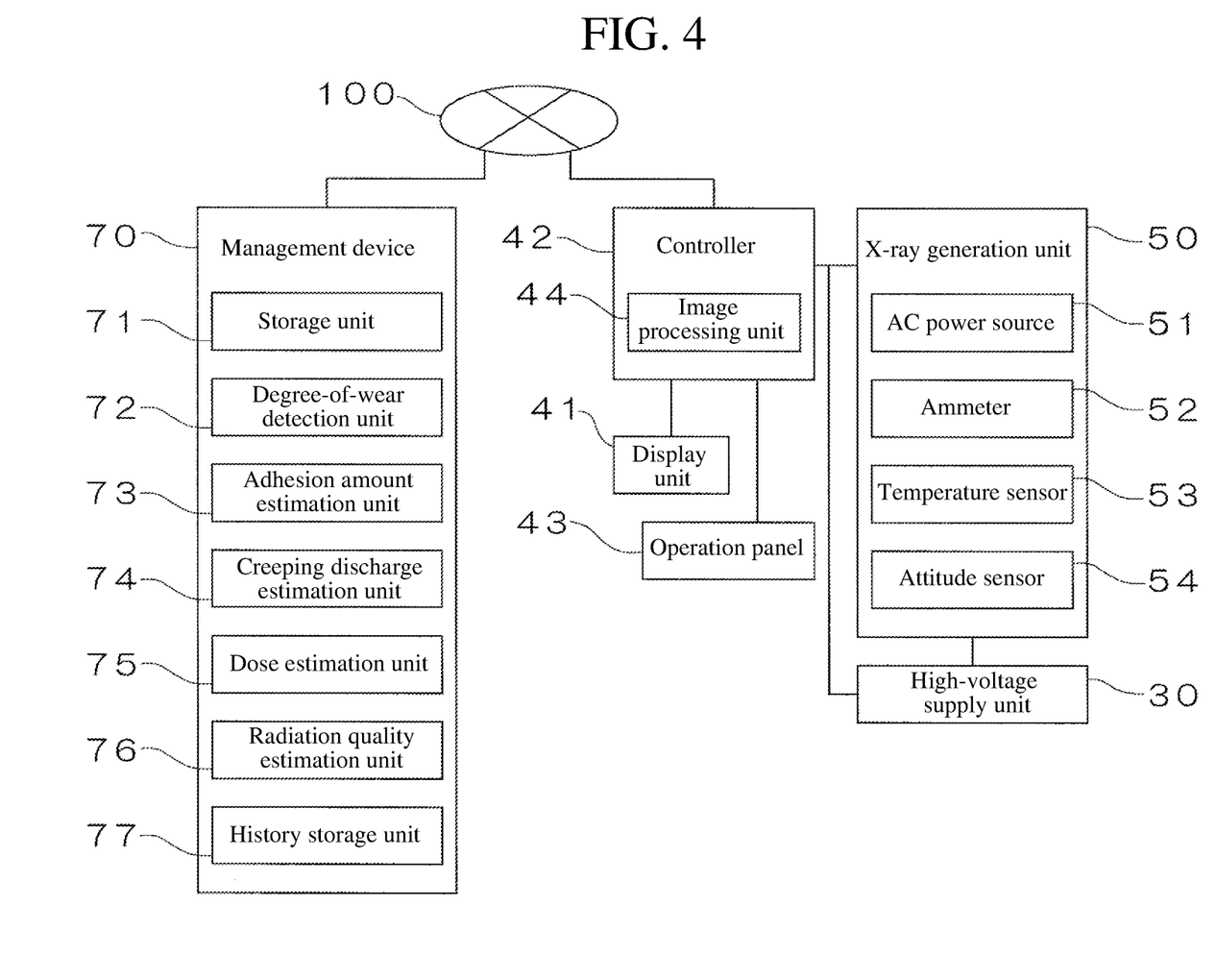
FIG. 4 is a diagram showing a main control system of the X-ray device according to the present invention.

FIG. 4 is a diagram showing the main control system of the X-ray device according to the present invention.

The X-ray device according to the present invention has a configuration in which a controller 42 of the X-ray fluoroscopic imaging apparatus shown in FIG. 1 and a management device 70 for managing the X-ray generation unit 50, etc., in the X-ray fluoroscopic imaging apparatus, are connected via a network 100, such as, e.g., the Internet or an intranet. The management device 70 is connected to a plurality of X-ray fluoroscopic imaging apparatuses via the network 100 and manages the operation status, the failure status, etc., of each of the X-ray fluoroscopic imaging apparatuses. Note that instead of using the management device 70 connected via the network 100, it may be configured such that the X-ray fluoroscopic imaging apparatus itself may have a management function equivalent to the management device 70.

The controller 42 shown in FIG. 1 and FIG. 4 is connected to an X-ray generation unit 50 and a high-voltage supply unit 30. The controller 42 is provided with an image processing unit 44 for processing the X-ray image captured by the X-ray detector 14 to display the processed image on the display unit 41. This controller 42 is composed of a computer with software installed. The controller 42 includes a processor (CPU), and the processor executes the processing for displaying the X-ray image captured by the X-ray detector 14 to display the image on the display unit 41.

The management device 70 is constituted by a computer with software installed. The functions of each part included in the management device 70 are realized by executing the software installed in the computer.

The management device 70 is provided with a storage unit 71. The storage unit 71 is configured to store: the relation between the degree-of-wear of the emitter 57 and the adhesion amount of the conductive material constituting the emitter 57 onto the envelope 60; the relation between the adhesion amount of the conductive material constituting the emitter 57 onto the envelope 60 and the probability of occurrence of a creeping discharge to the envelope 60; the relation between the adhesion amount of the conductive material constituting the emitter 57 onto the envelope 60 and the transmission rate of the X-rays passing through the envelope 60; or the relation between the adhesion amount of the conductive material constituting the emitter 57 onto the envelope 60 and the spectrum of the X-rays passing through the envelope 60.

Figure 5:
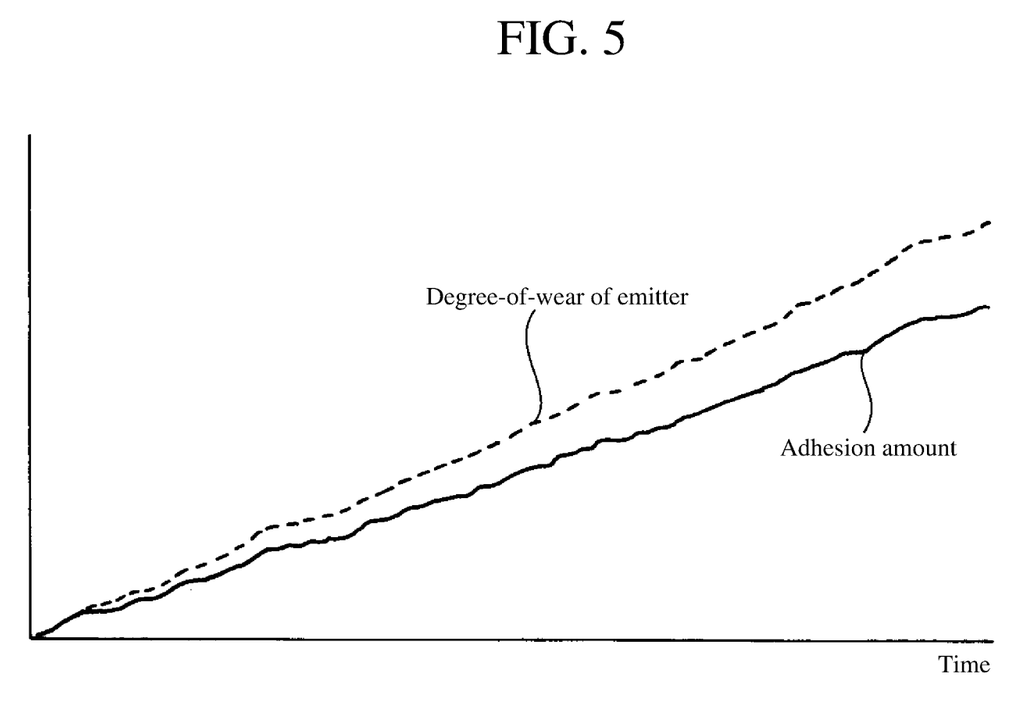
FIG. 5 is a graph showing a relation between a degree-of-wear of an emitter 57 and an adhesion amount of a conductive material constituting the emitter 57 onto an envelope 60.
Figure 6:
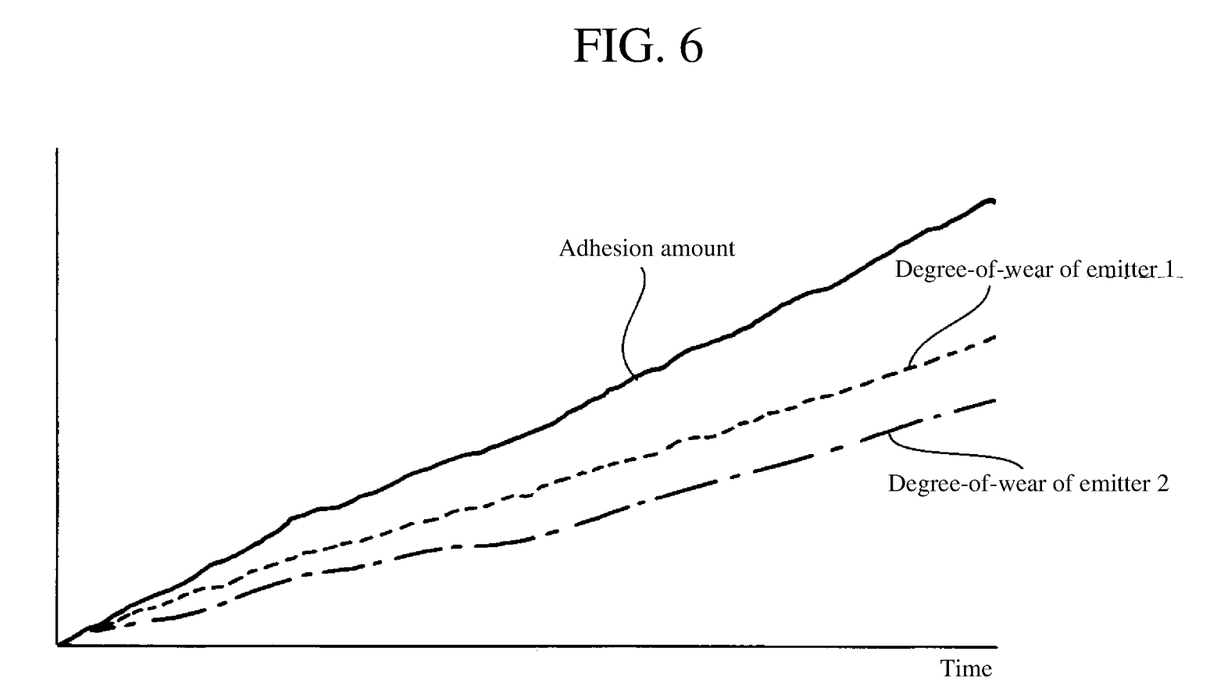
FIG. 6 is a graph showing a relation between a degree-of-wear of the emitter 57 and an adhesion amount of a conductive material constituting the emitter 57 onto the envelope 60.
Figure 7:
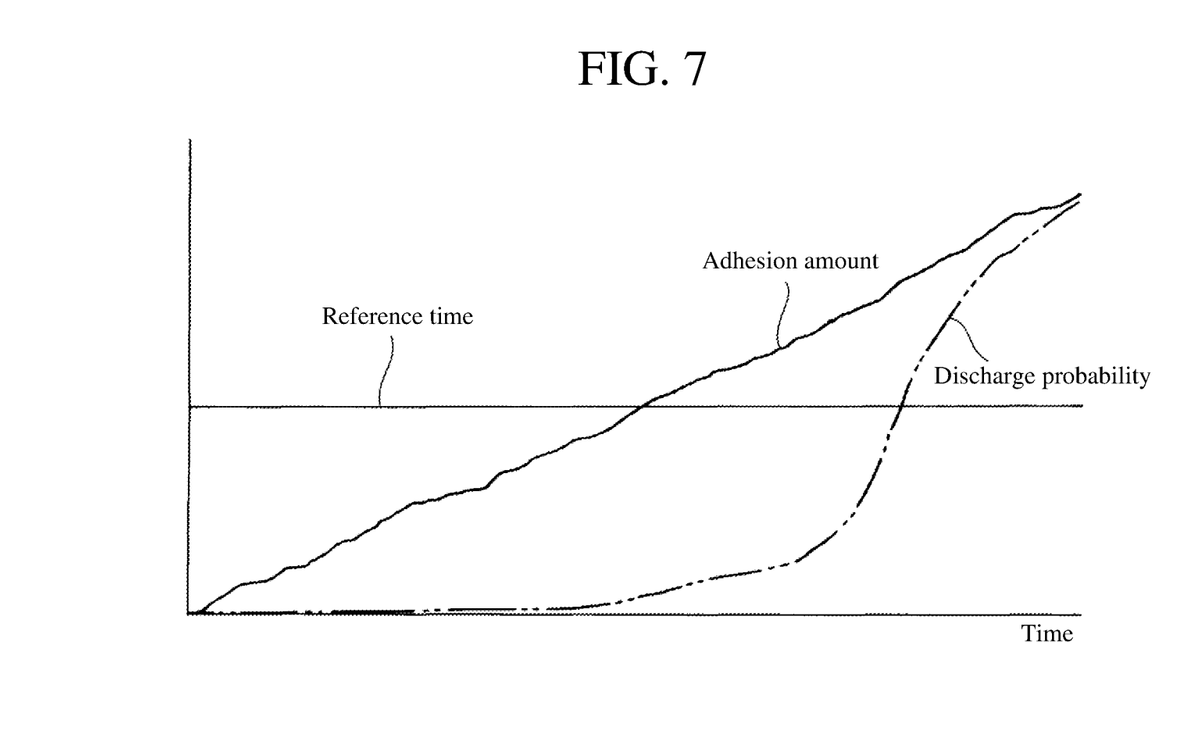
FIG. 7 is a graph showing a relation between an adhesion amount of a conductive material constituting the emitter 57 onto the envelope 60 and a probability of occurrence of a creeping discharge to the envelope 60.

FIG. 5 and FIG. 6 are graphs showing the relation between the degree-of-wear of the emitter 57 and the adhesion amount of the conductive material constituting the emitter 57 onto the envelope 60. Note that FIG. 5 shows the case in which a single emitter 57 is provided. FIG. 6 shows the case in which a plurality of emitters 57, such as, e.g., an emitter for a large focus and an emitter for a small focus, is provided. As shown in these figures, as the degree-of-wear of the emitter 57 increases, the adhesion amount of the conductive material constituting the envelope 60 increases. FIG. 7 is a graph showing the relation between the adhesion amount of the conductive material constituting the emitter 57 onto the envelope 60 and the probability of occurrence of a creeping discharge to the envelope 60. As shown in this diagram, when the adhesion amount of the conductive material constituting the emitter 57 onto the envelope 60 becomes a certain value or more, the probability of occurrence of a creeping discharge rapidly increases. Note that the data shown in FIG. 5 to FIG. 7 is experimentally obtained in advance and stored in the storage unit 71.

Referring again to FIG. 4, the management device 70 is provided with a degree-of-wear detection unit 72, an adhesion amount estimation unit 73, and a creeping discharge estimation unit 74. The degree-of-wear detection unit 72 is configured to detect the degree-of-wear of the emitter 57 from the voltage, the current, or the energization time (the cumulative energization time weighted by the current value) of the emitter 57. The adhesion amount estimation unit 73 is configured to estimate the adhesion amount of the conductive material onto the envelope 60 based on the degree-of-wear of the emitter 57 and the relation between the degree-of-wear of the emitter 57 and the adhesion amount of the conductive material onto the envelope 60 stored in the storage unit 71. The creeping discharge estimation unit 74 is configured to estimate the probability of occurrence of a creeping discharge based on the degree-of-wear of the emitter 57 and the relation between the adhesion amount of the conductive material onto the envelope 60 and the probability of occurrence of a creeping discharge to the envelope 60 stored in the storage unit 71. The management device 70 is provided with a processor (CPU), and the processor performs the following processing. That is, the processor performs the processing for detecting the degree-of-wear of the emitter 57 from the voltage, the current, or the energization time of the emitter 57. The processor also performs the processing of estimating the adhesion amount of the conductive material onto the envelope 60 based on the degree-of-wear of the emitter 57 and the relation between the degree-of-wear of the emitter 57 and the adhesion amount of the conductive material onto the envelope 60 stored in the storage unit 71. The processor also performs the processing of estimating the probability of occurrence of a creeping discharge based on the degree-of-wear of the emitter 57, and the relation between the degree-of-wear of the emitter 57 and the adhesion amount of the conductive material onto the envelope 60 stored in the storage unit 71, and the relation between the adhesion amount of the conductive material onto the envelope 60 and the probability of occurrence of creeping discharge to the envelope 60 stored in the storage unit 71.

Further, the management device 70 is provided with a dose estimation unit 75 and a radiation quality estimation unit 76. The dose estimation unit 75 is configured to estimate the dose of the X-rays emitted from the X-ray generation unit 50 based on the adhesion amount of the conductive material onto the envelope 60 and the relation between the adhesion amount of the conductive material to the envelope 60 and the transmission rate of the X-rays passing through the envelope 60. The radiation quality estimation unit 76 is configured to estimate the radiation quality of the X-rays emitted from the X-ray generation unit 50 based on the relation between the adhesion amount of the conductive material onto the envelope 60 and the spectrum of the X-rays passing through the envelope 60. The dose estimated by the dose estimation unit 75 and the radiation quality estimated by the radiation quality estimation unit 76 are transmitted to the image processing unit 44 in the controller 42. The image processing unit 44 changes the image processing condition of the X-ray image to be displayed on the display unit 41 based on the data of the dose and the data of the radiation quality. That is, the processor of the management device 70 performs the processing of estimating the dose of the X-rays emitted from the X-ray generation unit 50 based on the adhesion amount of the conductive body onto the envelope 60 and the relation between the adhesion amount of the conductive material onto the envelope 60 and the transmission rate of the X-rays passing through the envelope 60. The processor of the management device 70 also performs the processing of estimating the radiation quality of the X-rays emitted from the X-ray generation unit 50 based on the relation between the adhesion amount of the conductive material onto the envelope 60 and the spectrum of the X-rays passing through the envelope 60. The processor in the controller 42 executes the processing of changing the image processing condition of the X-ray image to be displayed on the display unit 41 based on the data of the dose and the data of the radiation quality.

Furthermore, the management device 70 is provided with a history storage unit 77 for storing the history of the use of the X-ray generation unit 50, the current value and the tube voltage of the emitter 57, the degree-of-wear of the emitter 57, the adhesion amount of the conductive material onto the envelope 60, and the like.

When performing the X-ray imaging by the X-ray device having the above-described configuration, the X-ray generation unit 50 and the collimator 12 are set to a predetermined attitude by swinging them with respect to the support 17 or rotating the support 17 in accordance with the imaging condition. The attitude of the X-ray generation unit 50 at this time is detected by the attitude sensor 54, such as, e.g., an accelerometer. The temperature of the X-ray generation unit 50 is measured by the temperature sensor 53. In this state, X-ray imaging is performed by emitting X-rays from the X-ray generation unit 50.

When the X-rays are being emitted from the X-ray generation unit 50, the current flowing through the emitter 57 is measured by the ammeter 52 and transmitted to the management device 70 via the network 100 along with the data of the tube voltage. Further, the data of the attitude of the X-ray generation unit 50 and the data of the temperature of the X-ray generation unit 50 are also transmitted to the management device 70 via the network 100.

The degree-of-wear detection unit 72 in the management device 70 detects the degree-of-wear of the emitter 57 from the data of the current flowing through the emitter 57 measured by the ammeter 52. Then, the adhesion amount estimation unit 73 in the management device 70 estimates the adhesion amount of the conductive material onto the envelope 60 based on the degree-of-wear of the emitter 57 and the relation between the degree-of-wear of the emitter 57 and the adhesion amount of the conductive material constituting the emitter 57 onto the envelope 60 stored in the storage unit 71.

When estimating the adhesion amount of the conductive material, the temperature data of the X-ray generation unit 50 and the attitude data of the X-ray generation unit 50 are taken into account. That is, the higher the temperature of the X-ray generation unit 50 is, i.e., the higher the temperature of the hydraulic fluid in the X-ray generation unit 50 or the temperature of the envelope 60 is, the adhesion amount of the conductive material onto envelope 60 is reduced. Depending on the attitude of the X-ray generation unit 50, the temperature of the X-ray generation unit 50 measured by the temperature sensor 53 varies greatly. For this reason, when estimating the adhesion amount of the conductive material, the temperature data of the X-ray generation unit 50 and the attitude data of the X-ray generation unit 50 are taken into account.

The creeping discharge estimation unit 74 in the management device 70 estimates the probability of occurrence of a creeping discharge based on: the degree-of-wear of the emitter 57, the relation between the degree-of-wear of the emitter 57 and the adhesion amount of the conductive material constituting the emitter 57 onto the envelope 60 stored in the storage unit 71; and the relation between the adhesion amount of the conductive material configuring the emitter 57 onto the envelope 60 and the probability of occurrence of a creeping discharge to the envelope 60 stored in the storage unit 71.

When the discharging probability exceeds the reference value shown in FIG. 7, the management device 70 performs a warning display with respect to the display unit 41 of the X-ray fluoroscopic imaging apparatus. This warning display indicates that the possibility of occurrence of a creeping discharge is high. At this time, it may be configured such that a warning display for prompting the execution of the seasoning (aging) is also displayed on the display unit 41.

Various data, such as, e.g., the data of the degree-of-wear of the emitter 57, the data of the adhesion amount of the conductive material onto the envelope 60 data, and the data of the probability of occurrence of a creeping discharge, when continuing X-ray imaging, are continuously stored in the history storage unit 77. In a case of performing a warning display, the contents of the warning display may be estimated by referring to the past various data as required.

Further, in parallel with this, when X-rays are being emitted from the X-ray generation unit 50, the dose estimation unit 75 estimates the dose of the X-rays emitted from the X-ray generation unit 50, based on the adhesion amount of the conductive material onto the envelope 60, and the relation between the adhesion amount of the conductive material onto the envelope 60 and the transmission rate of the X-rays passing through the envelope 60 stored in the storage unit 71. The radiation quality estimation unit 76 estimates the radiation quality of the X-rays emitted from X-ray generation unit 50 based on the relation between the adhesion amount of the conductive material onto the envelope 60 and the spectrum of the X-rays passing through the envelope 60 stored in the storage unit 71.

When the conductive material is adhered to the envelope 60, a part of the X-rays passing through the envelope 60 may be blocked or the spectrum of the X-rays may be changed. Therefore, the data of the dose of the X-rays and the data of the radiation quality of the X-rays are transmitted to the controller 42 in the X-ray fluoroscopic imaging apparatus. Then, the image processing unit 44 in the controller 42 changes the image processing condition, such as, e.g., the brightness and/or the contrast of the X-ray image to be displayed on the display unit 41 based on the dose data and the radiation quality data. With this, an X-ray image to be displayed on the display unit 41 can be made appropriate.

Note that the above-described embodiment has a configuration as the X-ray device according to the present invention in which the fluoroscopic imaging apparatus and the management device 70 are connected to each other via the network 100. However, the management device 70 may be directly connected to a fluoroscopic imaging apparatus, and each configuration in the management device 70 may be incorporated within the controller in a fluoroscopic imaging apparatus.

In the above-described embodiment, the probability of occurrence of a creeping discharge is estimated based on the degree-of-wear of the emitter 57, the relation between the degree-of-wear of the emitter 57 and the adhesion amount of the conductive material onto the envelope 60 stored in the storage unit 71, and the relation between the adhesion amount of conductive material onto the envelope 60 and the probability of occurrence of a creeping discharge to the envelope 60 stored in the storage unit 71. However, it may be configured such that by combining these two relations, the relation between the degree-of-wear of the emitter 57 and the probability of occurrence of a creeping discharge to the envelope 60 is obtained in advance, and the creeping discharge estimation unit 74 performs a warning or the like based on the relation between the degree-of-wear of the emitter 57 and the probability of occurrence of a creeping discharge to the envelope 60.

DESCRIPTION OF SYMBOLS

12: Collimator
13: Top board
14: X-ray detector
30: High-voltage supply unit
41: Display unit
42: Controller
43: Operation panel
44: Image processing unit
50: X-ray generation unit
51: AC power source
52: Ammeter
53: Temperature sensor
54: Attitude sensor
70: Management device
71: Storage unit
72: Degree-of-wear detection unit
73: Adhesion amount estimation unit
74: Creeping discharge estimation unit
75: Dose estimation unit
76: Radiation quality estimation unit
77: History storage unit
D: Operator
M: Subject
R1: Operating room
R2: Examination room

The invention claimed is:

1. An X-ray device comprising:
   an X-ray generation unit including an emitter made of a conductive material, the emitter being configured to emit electrons, a target for generating X-rays by being collided by the electrons emitted from the emitter, and an envelope accommodating the emitter and the target;
   a degree-of-wear detection unit configured to detect a degree-of-wear of the emitter;
   a storage unit configured to store a relation between the degree-of-wear of the emitter and an adhesion amount of the conductive material constituting the emitter onto the envelope; and
   an adhesion amount estimation unit configured to estimate the adhesion amount of the conductive material constituting the emitter onto the envelope based on the degree-of-wear of the emitter and a relation between the degree-of-wear of the emitter and the adhesion amount of the conductive material constituting the emitter stored in the storage unit.

2. The X-ray device as recited in claim 1,
   wherein the degree-of-wear detection unit detects the degree-of-wear of the emitter from a voltage, a current, or an energization time of the emitter.

3. The X-ray device as recited in claim 1, further comprising:
a temperature sensor,
wherein the adhesion amount estimation unit estimates the adhesion amount of the conductive material constituting the emitter onto the envelope by utilizing a temperature of the X-ray generation unit or a temperature of an insulation oil in the X-ray generation unit detected by the temperature sensor.

4. The X-ray device as recited in claim 1, further comprising:
an attitude sensor configured to detect an attitude of the X-ray generation unit,
wherein the adhesion amount estimation unit estimates the adhesion amount of the conductive material constituting the emitter onto the envelope by utilizing the attitude of the X-ray generation unit detected by the attitude sensor.

5. The X-ray device as recited in claim 1,
wherein the storage unit further stores a relation between the adhesion amount of the conductive material constituting the emitter onto the envelope and a probability of occurrence of a creeping discharge onto the envelope, and
wherein the X-ray device further comprises a creeping discharge estimation unit configured to estimate the probability of occurrence of the creeping discharge based on the degree-of-wear of the emitter, the relation between the degree-of-wear of the emitter and the adhesion amount of the conductive material constituting the emitter stored in the storage unit, and a relation between the adhesion amount of the conductive material constituting the emitter onto the envelope and the probability of occurrence of the creeping discharge onto the envelope stored in the storage unit.

6. The X-ray device as recited in claim 5,
wherein when the probability of occurrence of the creeping discharge estimated by the creeping discharge estimation unit exceeds a preset value, a warning display is performed.

7. The X-ray device as recited in claim 1,
wherein the storage unit further stores a relation between the adhesion amount of the conductive material constituting the emitter onto the envelope and a transmission rate of the X-rays passing through the envelope, or a relation between the adhesion amount of the conductive material constituting the emitter onto the envelope and a spectrum of the X-rays passing through the envelope, and
wherein the X-ray device further comprises an image processing unit configured to change an image processing condition of an X-ray image to be displayed on a display unit based on the adhesion amount of the conductive material constituting the emitter onto the envelope and, a relation between the adhesion amount of the conductive material constituting the emitter onto the envelope and the transmission rate of the X-rays passing through the envelope stored in the storage unit or a relation between the adhesion amount of the conductive material constituting the emitter onto the envelope and a spectrum of the X-rays passing through the envelope stored in the storage unit.

* * * * *